(12) United States Patent
Betzold et al.

(10) Patent No.: US 7,123,964 B2
(45) Date of Patent: Oct. 17, 2006

(54) REPLACEMENT INDICATOR TIMER FOR IMPLANTABLE MEDICAL DEVICES

(75) Inventors: Robert A. Betzold, Fridley, MN (US); James W. Busacker, St. Anthony, MN (US)

(73) Assignee: Medtronic, Inc., Minneapolis, MN (US)

( * ) Notice: Subject to any disclaimer, the term of this patent is extended or adjusted under 35 U.S.C. 154(b) by 512 days.

(21) Appl. No.: 10/367,316

(22) Filed: Feb. 15, 2003

(65) Prior Publication Data
US 2004/0162592 A1 Aug. 19, 2004

(51) Int. Cl.
*A61N 1/37* (2006.01)
(52) U.S. Cl. ...................................................... 607/29
(58) Field of Classification Search ................ 607/29
See application file for complete search history.

(56) References Cited

U.S. PATENT DOCUMENTS

| | | | |
|---|---|---|---|
| 5,228,439 A * | 7/1993 | Mann et al. | 607/29 |
| 5,370,668 A | 12/1994 | Shelton et al. | |
| 5,620,474 A * | 4/1997 | Koopman | 607/29 |
| 6,016,448 A | 1/2000 | Busacker et al. | |
| 6,108,579 A * | 8/2000 | Snell et al. | 607/29 |
| 6,154,675 A | 11/2000 | Juran et al. | |

\* cited by examiner

*Primary Examiner*—Jeffrey R. Jastrzab
(74) *Attorney, Agent, or Firm*—Girma Wolde-Michael; Paul H. McDowall

(57) ABSTRACT

A system and method is provided for reliably indicating that an implantable medical device is in need of replacement. The system and method measures the operational characteristics of the battery and the operational parameters of the implantable device itself. When these characteristics and parameters reach a defined level, the implantable medical device starts a replacement indicator timer. The replacement indicator timer starts and counts a replacement time period, with the replacement time period ending at a determined replacement date. The determined replacement date is the date at which the implantable medical device should be replaced.

35 Claims, 3 Drawing Sheets

100

REPLACEMENT INDICATOR TIMER FOR IMPLANTABLE MEDICAL DEVICES

FIELD OF THE INVENTION

This invention generally relates to implantable medical devices, and more specifically relates to implantable cardiac devices.

BACKGROUND OF THE INVENTION

A wide assortment of implantable medical devices are presently known and commercially available. These implantable medical devices include a variety of implantable cardiac devices. For example, implantable pulse generators (IPGs) are a type of cardiac device that is generally used to elevate the heart rate that is beating too slow. This type of device is sometimes referred to as a Bradycardia device or a pacemaker. Another type of implantable cardiac device is implantable cardiac defibrillators (ICDs). This type of device, often referred to as a Tachycardia device, is generally used to provide burst pacing pulses or a defibrillators shock to the heart when the heart is beating too fast. Another type of device is a cardiac resynchronization device used to treat heart failure.

Most implantable medical devices are contained within a hermetically sealed enclosure, in order to protect the operational components of the device from the harsh in-vivo environment, as well as to protect the body from the device. Typically it is necessary to provide an implantable medical device with a source of power, e.g., a battery, housed within the hermetic enclosure of the device. Battery longevity is often a critical consideration in the design and implementation of body implantable devices. It is highly impractical to replace the battery of the implanted medical device and it is clearly desirable to require replacement of the implanted device—a surgical procedure—as infrequently as possible.

Furthermore, notwithstanding the various measures that can be taken to maximize battery longevity, battery depletion is inevitable and many implantable medical devices are designed to account for this. For example, many implantable medical devices are provided with the ability to communicate an "elective replacement indicator" (ERI). The ERI informs the clinician that the device's power supply is nearing, but has not yet reached end-of-life (EOL), the point at which the power supply cannot provide sufficient energy to keep the device operable. The advance warning provided by an ERI gives the clinician the opportunity to take appropriate measures, e.g., to replace the device prior to EOL. Additionally, the implantable medical device may itself turn off various features, processors or therapies to save power in response to the ERI.

One current problem with implantable medical devices is that the ERI predictor may in some cases incorrectly indicate that replacement does not need to occur when it in fact it does. In other cases, the ERI predictor may indicate that replacement needs to occur when it does not. This is generally the case where the ERI is based on statistical calculations and various battery depletion metrics that have a relatively high degree of error between the prediction and the actual ERI event. This incorrect estimation of the battery life can lead to unexpected loss of device functionality which may be a serious medical event. Other errors may lead to premature replacement of the device.

Thus, what is needed is an improved, accurate system and method determining when to replace an implantable medical device.

BRIEF SUMMARY OF THE INVENTION

The present invention provides system and method for reliably indicating that an implantable medical device is in need of replacement. The system and method measures the operational characteristics of the battery and the operational parameters of the implantable device itself. When these characteristics and parameters reach a defined level, the implantable medical device starts a replacement indicator timer. The replacement indicator timer starts and counts a replacement time period, with the replacement time period ending at a determined replacement date. The determined replacement date is the date at which the implantable medical device should be replaced.

The start of the timer is selected such that it can be relatively assured that sufficient power will be available to operate the implantable medical device to the determined replacement date. Furthermore, the replacement time period is preferably selected to be long enough such that it is highly probable that the patient will visit the clinician in time to discover that the replacement indicator timer has been activated before the determined replacement date is reached. Thus, the replacement indicator timer serves to provide early warning to a clinician that the implantable medical device is approaching the end of life. Furthermore, the replacement indicator timer provides the determined replacement date to the clinician, such that the clinician can accurately know the date by which the implantable medical device should be replaced.

The foregoing and other objects, features and advantages of the invention will be apparent from the following more particular description of a preferred embodiment of the invention, as illustrated in the accompanying drawings.

BRIEF DESCRIPTION OF DRAWINGS

The preferred exemplary embodiment of the present invention will hereinafter be described in conjunction with the appended drawings, where like designations denote like elements, and.

DETAILED DESCRIPTION OF THE INVENTION

The present invention provides system and method for reliably indicating that an implantable medical device is in need of replacement. The system and method measures the operational characteristics of the battery and the operational parameters of the implantable device itself. When these characteristics and parameters reach a defined level, the implantable medical device starts a replacement indicator timer. The replacement indicator timer starts and counts a replacement time period, with the replacement time period ending at a determined replacement date. The determined replacement date is the date at which the implantable medical device should be replaced.

Figure 1:
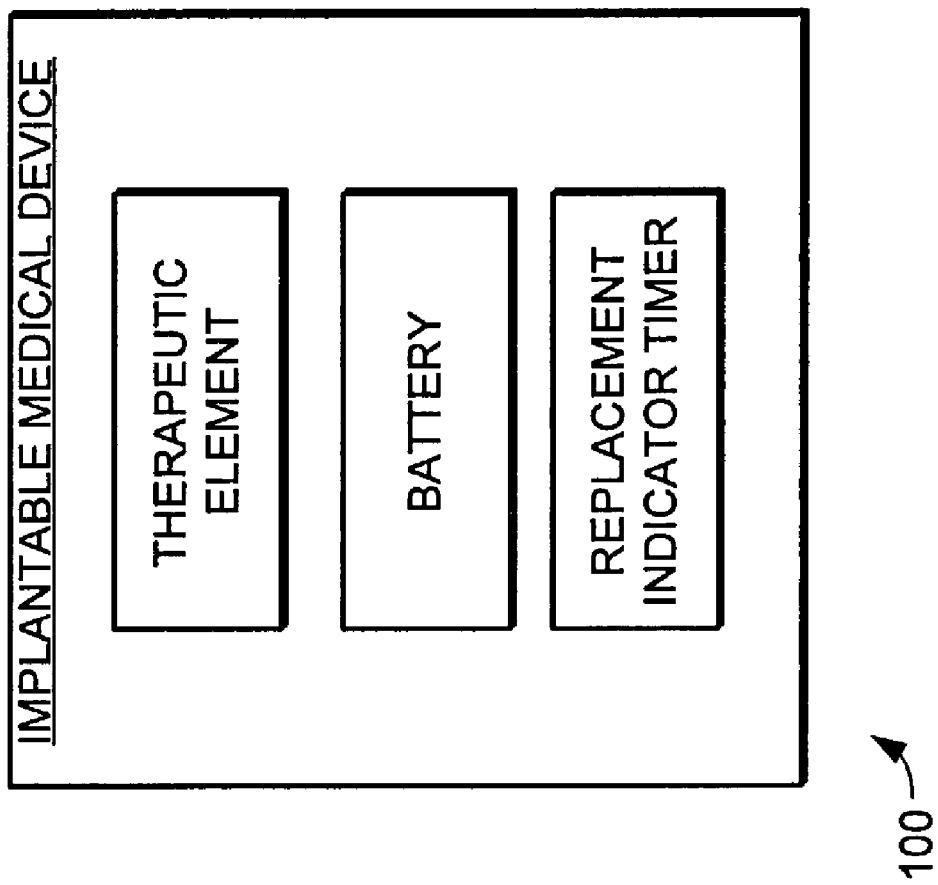
FIG. 1 is a schematic view of an implantable medical device.

Turning now to FIG. 1, an implantable medical device 100 is illustrated schematically. The implantable medical device 100 can be any type of implantable medical device, including implantable cardiac devices such as implantable pulse generators, implantable cardiac defibrillators and cardiac resynchronization devices. The implantable medical device 100 includes a therapeutic element, a battery, and a replacement indicator timer. The therapeutic element is broadly defined to be those elements of the implantable medical device 100 there to serve its medicinal purpose. As such, the therapeutic element can comprises a wide range of elements for a wide range of purposes, included the circuits and other devices that make up cardiac pacemakers, cardiac defibrillators, cardioverters, cardiac resynch ronization devices, neural stimulators, and many others. The battery is broadly defined as a power supply for the implantable medical device and thus can comprise any suitable power supply of any suitable construction and design.

The replacement indicator timer provides an indicator of when the implantable medical device is due for replacement. Specifically, the replacement indicator timer is started when the operational characteristics of the battery and the operational parameters of the implantable medical device indicate that the implantable medical device has a limited time period remaining. The replacement indicator timer counts through a replacement time period that ends at a determined replacement date.

The status of the replacement indicator timer is made available to the clinician or other monitor of the implantable medical device. The status of replacement indicator timer can be made available using any suitable system or method, so as such the non-invasive uplink and downlink communication channels that are commonly practiced in the art. In these systems a programming head or other instrument facilitates communication between the implanted medical device and the clinician, where the clinician is defined as any medical provider who is communicating with the device to monitor or control its function. The programming head is typically positioned on the patient's body such that one or more antennas with the head can send signals to and receive signals from the implantable medical device. As such, the status of the replacement indicator timer can be relatively easily provided to the clinician. The status can be provided to the clinician in the form of remaining time, or in the form of the determined replacement date, or any combination thereof.

In general, the operation of the replacement indicator timer is controlled by the selection of two main operational parameters. The first parameter is when to start the replacement indicator timer. The second is the length of time in the replacement time period, i.e., the time between the start of the replacement indicator timer and the determined replacement date. When configuring the operation of the implantable medical device, these parameters are interrelated and should be selected as such. In general, it is first desirable for the length of time in the replacement time period be of sufficient length to provide warning that replacement will be needed. Second, the start of the timer should be selected such that the sufficient power will be available to operate the implantable medical device, with some reserve provided for.

The length of time in the replacement time period counted by the replacement indicator timer is preferably selected according to several factors. It is generally desirable that the replacement time period be long enough such that it is highly probable that the patient will visit the clinician in time to discover that the replacement indicator timer has been activated before the determined replacement date is reached. This allows the replacement indicator timer to provide early warning to a clinician that the implantable medical device is approaching its end-of-life (EOL) as indicated by the determined replacement date. Furthermore, the replacement indicator timer provides the determined replacement date to the clinician, such that the clinician can accurately know the date by which the implantable medical device should be replaced. To effectively accomplish this, the replacement indicator timer needs to start early enough to allow a relatively long replacement time period to occur before the replacement date is reached.

In one example, the current clinical practice for some pacemakers is to recommend that the patient visit a clinician every six months to evaluate the pacemaker. In such a device, the length of replacement time period could be set to greater than six months to increase the likelihood that the patient will visit the clinician before the replacement time period ends. For example, the replacement time period could be set between nine and twelve months to achieve this result. The actual time selected would again depend on many factors, including the type, size and shape of the battery, and the power consumption of the device. In another example, the length of the replacement time period can be set by the clinician to a length that is appropriate for a particular patient. This can occur when the device is implanted, or in later diagnostic visits.

The start of the timer is preferably selected such that it can be relatively assured that sufficient power will be available to operate the implantable medical device 100 to the determined replacement date, with some margin of error provided for. The start of the timer would typically occur when a selected operational characteristic of the battery reaches a selected value. The operational characteristic monitored and the selected value used to trigger the start of the timer would typically depend on the type of the battery being used. Additionally, the selected value used to trigger the start of the timer could depend on the rate of power consumption in the implantable medical device, or other operational parameters of the implantable medical device.

In this embodiment, the start of the timer would be dependent upon the condition of the battery and rate of power consumption for the implantable medical device 100. When the condition of the battery indicates that that a certain amount of battery life exists under current power consumption conditions, the replacement indicator timer starts to count through the replacement time period.

It should be noted that providing for some reserve in the replacement timer period and the determined replacement date is generally desirable as it is preferred to have a more accurate predictor indicator at the expense of a relatively small extension of device life. This trade off is increasingly desirable in today's clinical environment where scheduling of a patient, surgeon, and operating room has a higher priority over an extra month or two of device longevity.

The parameters used to determine the start of the timer would depend upon the type of battery being used. Some may use battery impedance or output voltage exclusively, and others may use some specific combination of these parameters. For example, in lithium iodine batteries the impedance and battery voltage can be measured to trigger the start of the timer. In these applications, the trip voltage used to signify depletion of the battery changes as the output impedance rises. Thus, the combination of output voltage and impedance is used to determine an estimation of remaining battery life. See U.S. Pat. No. 6,016,448 issued to Busacker et al and assigned to Medtronic, Inc., for a more detailed explanation of how such a system can work. Such a system can be adapted to determine the starting point of the replacement indicator timer.

Figure 2:
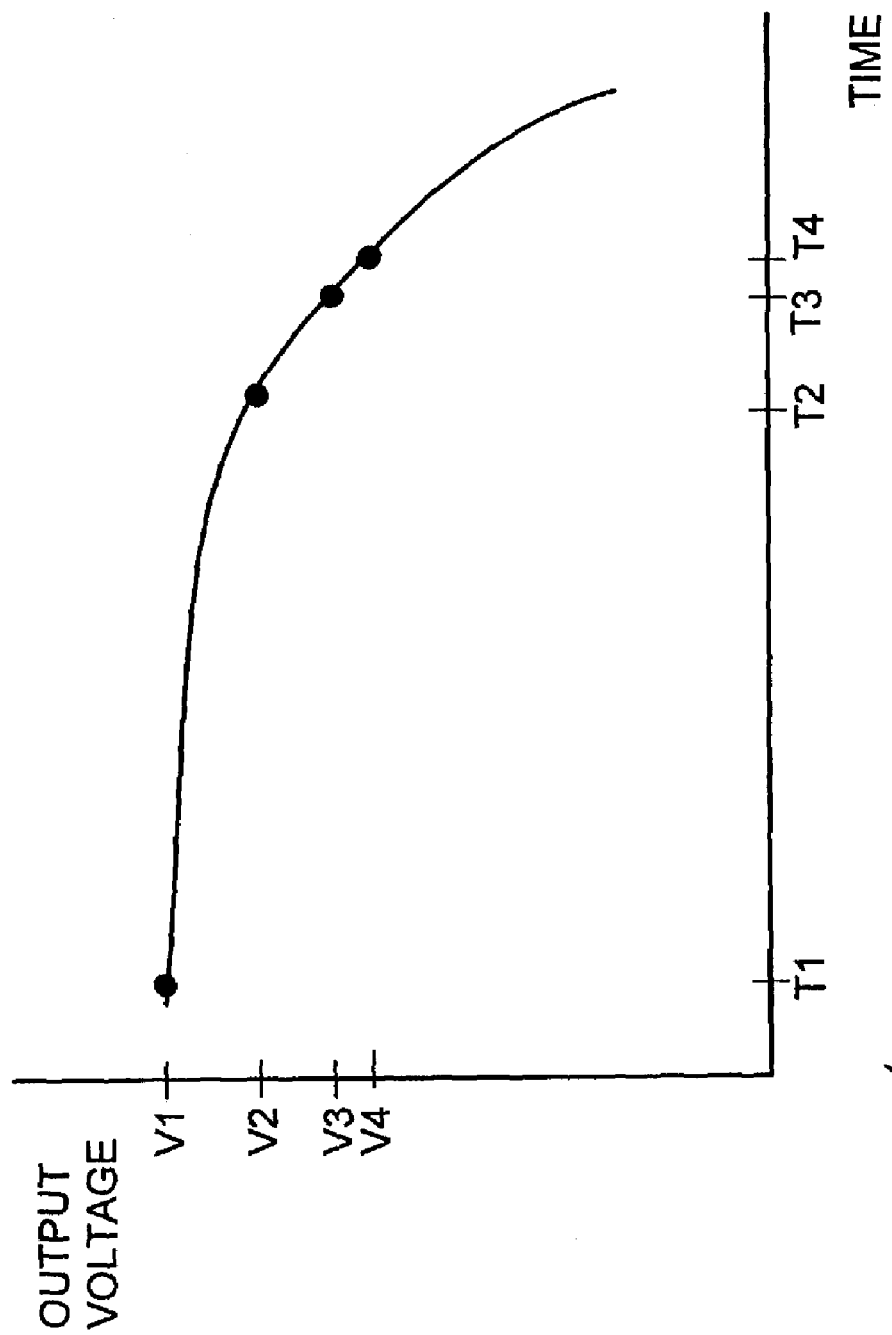
FIG. 2 is a graph of battery output voltage as a function of time for an exemplary implantable medical device.

Turning now to FIG. 2, a graph 200 of battery output voltage as a function of time for an exemplary implantable medical device is illustrated. Graph 200 illustrates an example of how the battery output voltage decreases as the battery is used and how the battery voltage can be used to trigger the replacement indicator timer. This type of approach would generally be desirable in low impedance batteries such as lithium magnesium dioxide ($LiMnO_2$) or lithium silver vanadium oxide (LiSVO). In the illustrated example, the battery starts with a voltage of V1 at time T1. As time progresses, the battery voltage drops slightly. When the battery voltage reaches a defined level V2 (at time T2) the replacement indicator timer starts counting through the replacement time period. The replacement time period ends at time T3, with the battery voltage at V3. Thus, time T3 comprises the determined replacement date for this example, and the time between T2 and T3 comprises the replacement time period. Finally, the output voltage continues to drop until the device cannot continue to operate, the device end-of-life. In the illustrated example, the end-of-life occurs when the voltage drops to V4, at time T4. Again, the battery voltage used to start the replacement indicator timer (voltage V2) is preferably selected to ensure that the time T3 is reached before the device reaches its end of life, with some reserve.

Figure 3:
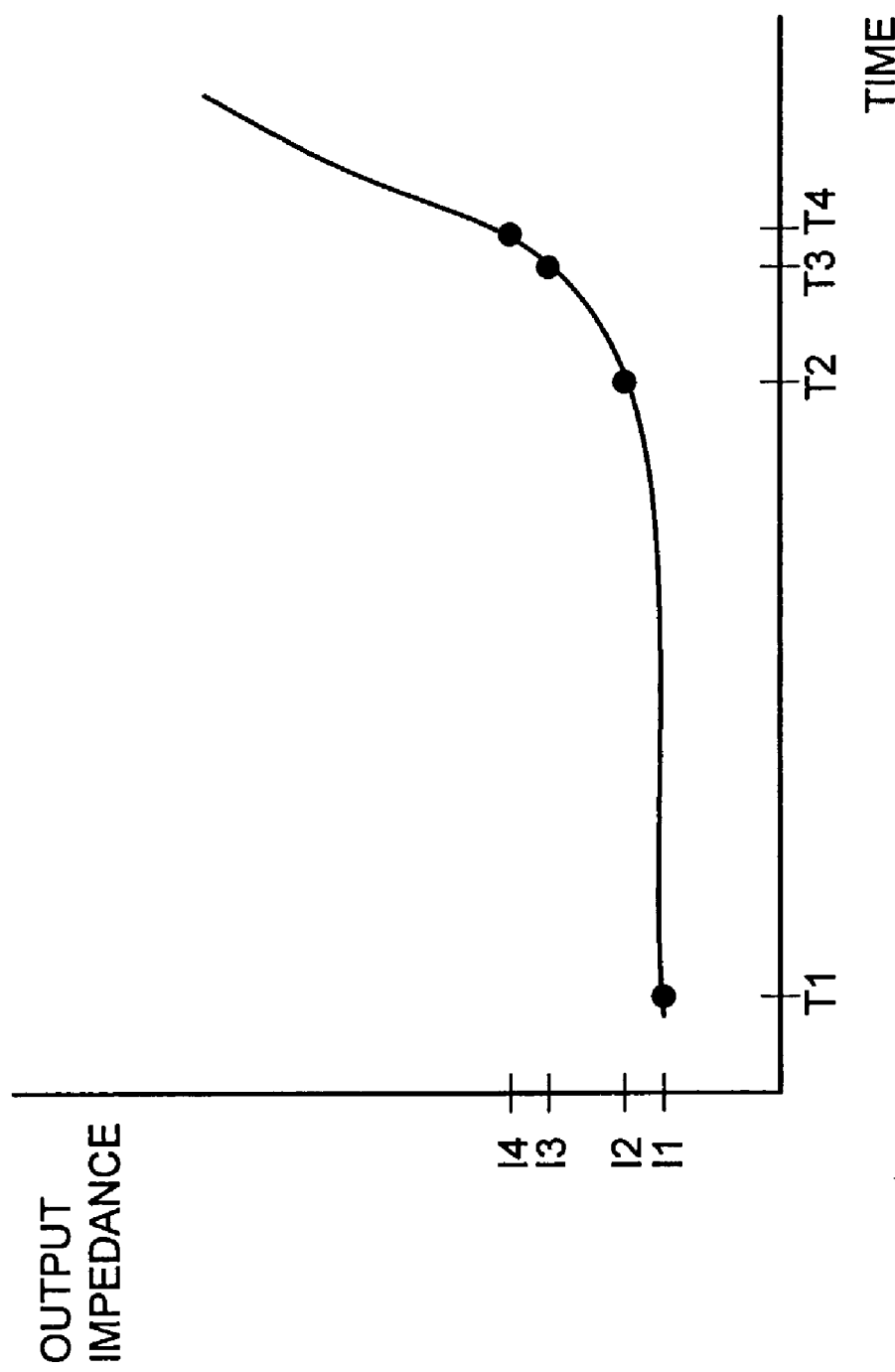
FIG. 3 is a graph of battery impedance as a function of time for an exemplary implantable medical device.

Turning now to FIG. 3, a graph 300 of battery impedance as a function of time for an exemplary implantable medical device is illustrated. Graph 300 illustrates an example of how the battery impedance increases as the battery is used and how this might be used to trigger the replacement indicator timer. This type of approach would generally be desirable for high impedance batteries such as lithium iodine (LiI). In the illustrated example, the battery starts with an impedance I1 at time T1. As time progresses, the battery impedance rises slightly. When the battery impedance reaches a defined level I2 (at time T2) the replacement indicator timer starts counting through the replacement time period. The replacement time period ends at time T3, with the battery impedance at I3. Again, time T3 comprises the determined replacement date for this example, and the time between T2 and T3 comprises the replacement time period. Finally, the output impedance continues to rise until the device cannot continue to operate, the device end-of-life. In the illustrated example, the end-of-life occurs when the impedance rises to I4, at time T4. Again, the battery impedance used to start the replacement indicator timer (impedance I2) is preferably selected to ensure that the time T3 is reached before the device reaches its end of life, with some reserve.

It should be noted that the selected value of the battery impedance I2 and the output voltage V2 used to trigger the start of the timer would depend upon the size and type of the battery. Furthermore, the selected value used to trigger the start of the timer could be dependent upon the rate of power consumption in the device. In this case, the implantable medical device could monitor power consumption and select a value to trigger the start of the timer based on the monitored power consumption.

In one embodiment of the invention the operation of the replacement indicator timer is varied when the operational parameters of the implantable medical device are changed. Thus, if upon discovery that the replacement indicator timer has been activated and the clinician changes the operational parameters of the implantable medical device, the replacement indicator timer can be automatically updated to reflect the new parameters. As such, the clinician can change the operational parameters to extend the life of the implantable medical device and immediately learn the effects of those changes on the replacement time period.

As one example, the timer can have a counting rate that varies on a scale of 1 to 4 depending upon the implantable medical device's use of battery energy per its programming settings, lead impedance, and percentage of pacing. As varying the counting rate necessarily changes the remaining replacement timer period and the corresponding determined replacement date, these changes are preferably made available to the clinician through the programming/communication link of the implantable medical device. Of course other methods can be used to vary the timer, such as by varying the defined end value of the timer.

Again, the changes in the counting rate, replacement timer period and new determined replacement date should be made to provide for a sufficient reserve to ensure that the implantable medical device lasts to the new determined replacement date.

In a further variation, the implantable medical device behavior at the determined replacement date can be in part determined by whether or not the replacement indicator timer has been accessed by the clinician. For example, if the replacement indicator timer has been accessed by a clinician, it can be assumed that the clinician is aware of the determined replacement date. Under those circumstances, the implantable medical device can continue to operate normally even after the replacement date has been reached. This can be safely done as it can be assumed that the clinician will soon replace the implantable medical device. If, on the other hand, the replacement indicator timer has not been accessed by a clinician when the determined replacement date is met, the implantable medical device can immediately go into low power operational mode to conserve power as long as possible.

Such a system can be implemented by storing within the device pertinent details from prior communications to the device. As such, the implantable medical device can store whether the device has been analyzed by a clinician since the start of the replacement indicator timer and operate accordingly. The occurrence of these follow-ups can be detected by relatively simple methods, such telemetry sessions or use more sophisticated methods such as telemetry interrogations. In further variations a more detailed accounting of patient follow-up care can be stored in the device and used to determine whether or not to operate in low power mode at the end of the replacement time period.

This system allows a patient to avoid having their implantable medical device go into low power mode when it will be replaced shortly. For example, in some pacemaker systems the pacemaker goes into a lower power mode when the battery power drops below a certain defined point. These low power modes shut down diagnostic logging functions and other non essential functions. In addition to going to a low power mode, the pacemaker can be made to pulse at a defined rate, such as 65 ppm, that offers a scaled-back form of therapy. One example of a low power mode for a pacemaker type device is a VVI mode. In a VVI mode only the ventricle is paced and sensed, and the pacemaker inhibits pacing if a ventricular sense occurs first. When operating in VVI mode, the pacemaker saves power but at the disadvantage of providing less functionality to the patient. In some patients however, the low power mode may lead to complications. Thus, it is desirable to avoid low power mode in these circumstances. Other types of devices have different low power modes, but many of these other low power modes also suffer from disadvantages.

The system described above has the advantage of eliminating the possibility of going into low power mode when it is known that the status of the device has been recently ascertained by the clinician. Here, it can be assumed that because the clinician has accessed the device and learned that the replacement indicator timer has started and thus learned the determined replacement date, that replacement is imminent. In this circumstance, the implantable medical device can be left to operate at full capacity or in some other pre-programmed mode. For example, a pacemaker may remain in a dual chamber mode, where both the ventricle and atrium are paced and sensed. The implantable medical device can be operating in this type of mode because it can be relatively safely assumed that the clinician will soon remove and replace the device. Thus, the patient does not have to deal with any complications that may arise from operation in low power mode.

If, on the other hand, no communication has been made to the implantable medical device, then the device can be put into low power mode at the determined replacement date. This increases the life of the device and thus increases the probability that the patient will visit the clinician to have the device analyzed before the battery is extinguished and all operation of the device stops.

In a further variation the implantable medical device behavior at the determined replacement date can be controlled by the clinician. For example, the implantable medical device can be configured to allow the clinician to choose whether the device continues to operate at full capacity or instead goes into a low power mode at the determined replacement date. This behavior could be selected when the device is implanted into the patient or at later follow-up visits with the clinician. For example, the choice can be given when the clinician accesses the device after the replacement indicator timer has started counting.

The present invention thus provides a system and method for reliably indicating that an implantable medical device is in need of replacement. The system and method measures the operational characteristics of the battery and the operational parameters of the implantable device itself. When these characteristics and parameters reach a defined level, the implantable medical device starts a replacement indicator timer. The replacement indicator timer starts and counts a replacement time period, with the replacement time period ending at a determined replacement date. The determined replacement date is the date at which the implantable medical device should be replaced.

The start of the timer is selected such that it can be relatively assured that sufficient power will be available to operate the implantable medical device to the determined replacement date. Furthermore, the replacement time period is preferably selected to be long enough such that it is highly probable that the patient will visit the clinician in time to discover that the replacement indicator timer has been activated before the determined replacement date is reached. Thus, the replacement indicator timer serves to provide early warning to a clinician that the implantable medical device is approaching the end of life. Furthermore, the replacement indicator timer provides the determined replacement date to the clinician, such that the clinician can accurately know the date by which the implantable medical device should be replaced.

The embodiments and examples set forth herein were presented in order to best explain the present invention and its particular application and to thereby enable those skilled in the art to make and use the invention. However, those skilled in the art will recognize that the foregoing description and examples have been presented for the purposes of illustration and example only. The description as set forth is not intended to be exhaustive or to limit the invention to the precise form disclosed. Many modifications and variations are possible in light of the above teaching without departing from the spirit of the forthcoming claims.

What is claimed is:

1. An implantable medical device, the implantable medical device comprising:
 a) a battery, the battery providing power to the implantable medical device;
 b) a replacement indicator timer, the replacement indicator timer counting a replacement time period to a determined replacement date for the implantable medical device, the replacement indicator timer starting the counting when an operational characteristic of the battery reaches a selected value; and
 c) means for automatically determining, once the replacement indicator timer begins counting, whether one of an interrogation of a device parameter and a reprogramming of an operational parameter have occurred.

2. The implantable medical device of claim 1 wherein the replacement time period is at least six months.

3. The implantable medical device of claim 1 wherein the replacement time period is between nine and twelve months.

4. The implantable medical device of claim 1 wherein the replacement time period is determined by a clinician.

5. The implantable medical device of claim 1 wherein the selected value of the operational characteristic of the battery is at least in part determined by an operational parameter of the implantable medical device.

6. The implantable medical device of claim 5 wherein the operational parameter of the implantable medical device comprises power consumption of the implantable medical device.

7. The implantable medical device of claim 1 wherein the implantable medical device communicates a status of the replacement indicator timer to a clinician during a communication procedure.

8. The implantable medical device of claim 1 wherein the implantable medical device operates in a lower power mode when the determined replacement date is reached.

9. The implantable medical device of claim 1 wherein the implantable medical device does not go into a lower power mode when the determined replacement date is reached if the implantable medical device has been interrogated or has been reprogrammed during the replacement time period.

10. The implantable medical device of claim 1 further comprising means for reprogramming the implantable medical device to operate in a relatively lower power mode when the determined replacement date is reached.

11. The implantable medical device of claim 1 wherein the replacement indicator timer varies a counting rate when an operation of the implantable medical device is modified by a clinician.

12. The implantable medical device of claim 1 wherein the replacement time period is varied when an operation of the implantable medical device is modified by a clinician.

13. The implantable medical device of claim 1 wherein the operational characteristic of the battery includes battery impedance.

14. The implantable medical device of claim 1 wherein the operational characteristic of the battery includes an output voltage.

15. The implantable medical device of claim 1 wherein the replacement time period and the determined replacement date are selected to provide a reserve to allow the implantable medical device to continue to operate past the determined replacement date with a defined level of confidence.

16. The implantable medical device of claim 1 wherein the implantable medical device comprises an implantable pulse generator.

17. The implantable medical device of claim 1 wherein the implantable medical device comprises a cardiac defibrillator.

18. The implantable medical device of claim 1 wherein the implantable medical device comprises a cardiac resynchronization device.

19. A method for providing notice to a clinician of a removal date for an implantable medical device, the method comprising the steps of:
   a) monitoring an operational characteristic of a battery in the implantable medical device during operation of the implantable medical device;
   b) starting a replacement indicator timer in the implantable medical device when the operational characteristic of the battery reaches a selected value;
   c) automatically determining if one of an interrogation of a device parameter and a reprogramming of an operational parameter have occurred;
   d) counting through a replacement time period with the replacement indicator timer to a determined replacement date; and
   e) communicating a status of the replacement indicator timer to the clinician.

20. The method of claim 19 wherein the replacement time period is at least six months.

21. The method of claim 19 wherein the replacement time period is between nine and twelve months.

22. The method of claim 19 wherein the replacement time period is determined by a clinician.

23. The method of claim 19 wherein the selected value of the operational characteristic of the battery is at least in part determined by an operational parameter of the implantable medical device.

24. The method of claim 23 wherein the operational parameter of the implantable medical device comprises power consumption of the implantable medical device.

25. The method of claim 19 further comprising the step of putting the implantable medical device into a lower power mode.

26. The method of claim 19 further comprising the step of not putting the implantable medical device into a lower power mode.

27. The method of claim 19 further comprising the step of a clinician selectively determining whether the implantable medical device goes into a lower power mode when the determined replacement date is reached.

28. The method of claim 19 further comprising the step of varying a counting rate of the replacement indicator timer when an operation of the implantable medical device is modified by a clinician.

29. The method of claim 19 further comprising the step of varying the replacement time period when an operating parameter of the implantable medical device has been reprogrammed.

30. The method of claim 19 wherein the operational characteristic of the battery includes battery impedance.

31. The method of claim 29 wherein the operational characteristic of the battery includes an output voltage.

32. The method of claim 29 further comprising the step of determining the replacement time period and the determined replacement date to provide a reserve to allow the implantable medical device to continue to operate past the determined replacement date with a defined level of confidence.

33. The method of claim 19 wherein the implantable medical device comprises an implantable pulse generator.

34. The method of claim 19 wherein the implantable medical device comprises a cardiac defibrillator.

35. The method of claim 19 wherein the implantable medical device comprises a cardiac resynchronization device.

* * * * *